(12) United States Patent
Zheng et al.

(10) Patent No.: US 7,916,919 B2
(45) Date of Patent: Mar. 29, 2011

(54) SYSTEM AND METHOD FOR SEGMENTING CHAMBERS OF A HEART IN A THREE DIMENSIONAL IMAGE

(75) Inventors: Yefeng Zheng, Plainsboro, NJ (US); Adrian Barbu, Tallahassee, FL (US); Bogdan Georgescu, Plainsboro, NJ (US); Michael Scheuering, Nürnberg (DE); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 839 days.

(21) Appl. No.: 11/856,878

(22) Filed: Sep. 18, 2007

(65) Prior Publication Data

US 2008/0101676 A1    May 1, 2008

Related U.S. Application Data (60) Provisional application No. 60/827,235, filed on Sep. 28, 2006, provisional application No. 60/913,353, filed on Apr. 23, 2007.

(51) Int. Cl.
*G06K 9/00* (2006.01)

(52) U.S. Cl. .......................... 382/131; 382/128; 382/159
(58) Field of Classification Search .................. 382/131
See application file for complete search history.

(56) References Cited

U.S. PATENT DOCUMENTS

| 7,792,342 B2 * | 9/2010 | Barbu et al. ................. 382/128 |
| 2003/0187358 A1 * | 10/2003 | Okerlund et al. ............. 600/443 |
| 2005/0031202 A1 * | 2/2005 | Accomazzi et al. .......... 382/173 |
| 2005/0281447 A1 * | 12/2005 | Moreau-Gobard et al. .. 382/130 |
| 2008/0101676 A1 * | 5/2008 | Zheng et al. ................. 382/131 |

OTHER PUBLICATIONS

Qian Z, Metaxas D, and Axel L, "A Learning Framework for the Automatic and Accurate Segmentation of Cardiac Tagged MRI Images." In Proc. of Computer Vision for Biomedical Image Applications Workshop, In Conjunction with ICCV, Lecture Notes in Computer Science 3765, pp. 93-102, Oct. 21, 2005.*

\* cited by examiner

*Primary Examiner* — Sath V Perungavoor (57) ABSTRACT

A system and method for segmenting chambers of a heart in three dimensional images is disclosed. A set of three dimensional images of a heart is received. The shape of the heart in the three dimensional images is localized. Boundaries of the chambers of the heart in the localized shape are identified using steerable features.

18 Claims, 8 Drawing Sheets

SYSTEM AND METHOD FOR SEGMENTING CHAMBERS OF A HEART IN A THREE DIMENSIONAL IMAGE

CROSS REFERENCE TO RELATED APPLICATION

This application claims the benefit of U.S. Provisional Application Ser. No. 60/827,235, filed Sep. 28, 2006 and Ser. No. 60/913,353, filed Apr. 23, 2007 which is are incorporated by reference in its their entirety.

FIELD OF THE INVENTION

The present invention is directed to a system and method for segmenting chambers of a heart in a three dimensional image, and more particularly, to a system and method for segmenting chambers of a heart in a three dimensional image using anatomical structure localization and boundary delineation.

BACKGROUND OF THE INVENTION

Cardiac computed tomography (CT) is an important imaging modality for diagnosing cardiovascular disease and it can provide detailed anatomic information about the cardiac chambers, large vessels or coronary arteries. Multi-chamber heart segmentation is a prerequisite for global quantification of the cardiac function. The complexity of cardiac anatomy, poor contrast, noise or motion artifacts makes this segmentation a challenging task. Most known approaches focus on only left ventricle segmentation. Complete segmentation of all four heart chambers can help to diagnose diseases in other chambers, e.g., left atrium fibrillation, right ventricle overload or to perform dyssynchrony analysis.

There are two tasks for a non-rigid object segmentation problem: object localization and boundary delineation. Most of the known approaches focus on boundary delineation based on active shape models, active appearance models, and deformable models. There are a few limitations inherent in these techniques: 1) Most of them are semiautomatic and manual labeling of a rough position and pose of the heart chambers is needed. 2) They are likely to get stuck in local strong image evidence. Other known techniques are straightforward extensions of two dimensional (2D) image segmentation to three dimensional (3D) image segmentation. The segmentation is performed on each 2D slice and the results are combined to get the final 3D segmentation. However, such techniques cannot fully exploit the benefit of 3D imaging in a natural way.

Object localization is required for an automatic segmentation system and discriminative learning approaches have proved to be efficient and robust for solving 2D problems. In these methods, shape detection or localization is formulated as a classification problem: whether an image block contains the target shape or not. To build a robust system, a classifier only has to tolerate limited variation in object pose. The object is found by scanning the classifier over an exhaustive range of possible locations, orientations, scales or other parameters in an image. This searching strategy is different from other parameter estimation approaches, such as deformable models, where an initial estimate is adjusted (e.g., using the gradient descent technique) to optimize a predefined objective function.

Exhaustive searching makes the system robust under local minima, however there are two challenges to extend the learning based approaches to 3D. First, the number of hypotheses increases exponentially with respect to the dimensionality of the parameter space. For example, there are nine degrees of freedom for the anisotropic similarity transformation, namely three translation parameters, three rotation angles and three scales. If n discrete values are searched for each dimension, the number of tested hypotheses is $n^9$ (for a very coarse estimation with a small n=5, $n^9$=1,953,125). The computational demands are beyond the capabilities of current desktop computers. Due to this limitation, previous approaches often constrain the search to a lower dimensional space. For example, only the position and isotropic scaling (4D) is searched in the generalized Hough transformation based approach. The second challenge is that efficient features are needed to search the orientation and scale spaces. Haar wavelet features can be efficiently computed for translation and scale transformations. However, when searching for rotation parameters, one either has to rotate the feature templates or rotate the volume which is very time consuming. The efficiency of image feature computation becomes more important when combined with a very large number of test hypotheses. There is a need for an approach for detecting shapes in high dimensional images that is efficient and less computationally intensive.

SUMMARY OF THE INVENTION

A system and method for segmenting chambers of a heart in three dimensional images is disclosed. A set of three dimensional images of a heart is received. The shape of the heart in the three dimensional images is localized. Boundaries of the chambers of the heart in the localized shape are identified using steerable features.

BRIEF DESCRIPTION OF THE DRAWINGS

Preferred embodiments of the present invention will be described below in more detail, wherein like reference numerals indicate like elements, with reference to the accompanying drawings.

DETAILED DESCRIPTION

Figure 1:
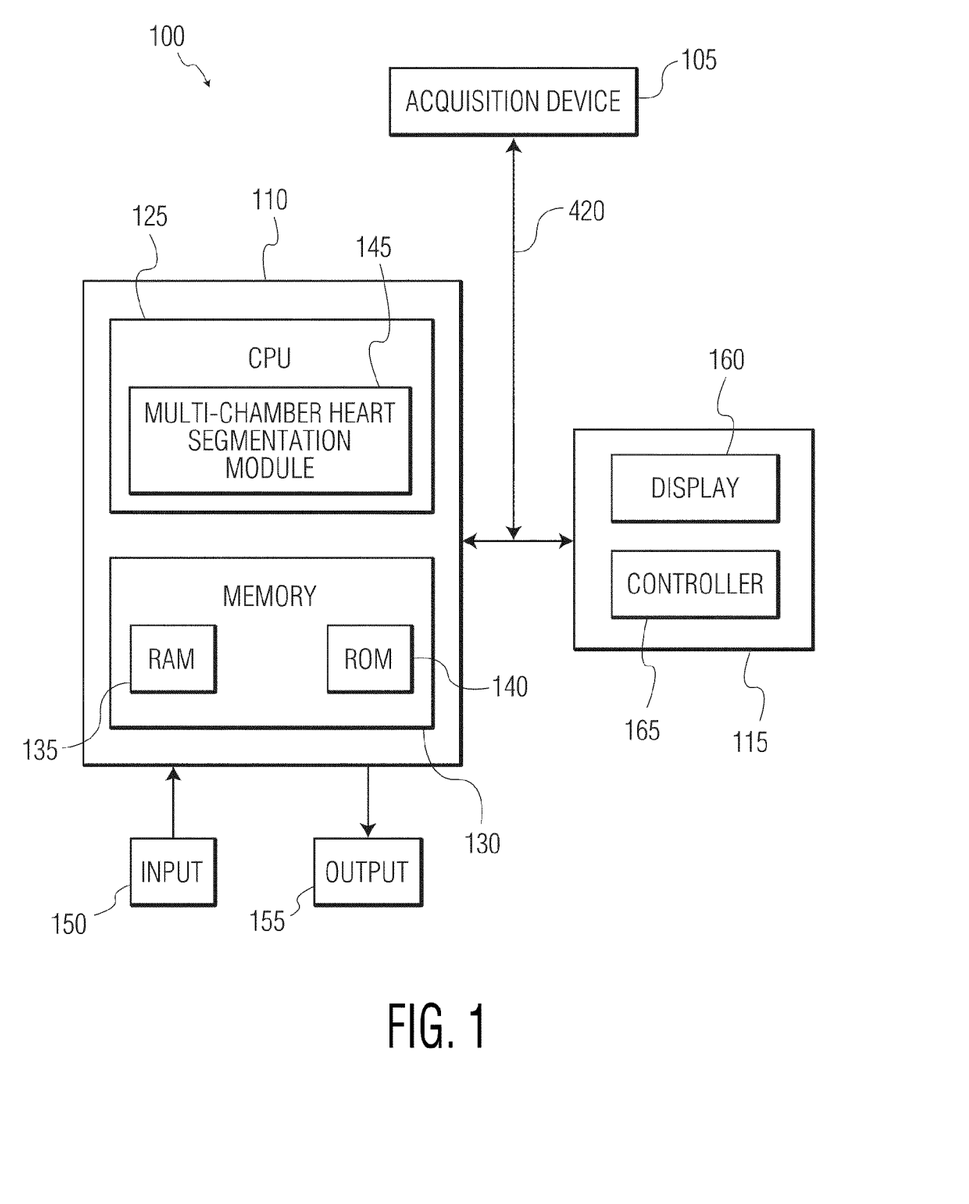
FIG. 1 is a block diagram of an exemplary system for implementing a segmentation of heart chambers in a three dimensional image in accordance with the present invention.
Figure 2A:
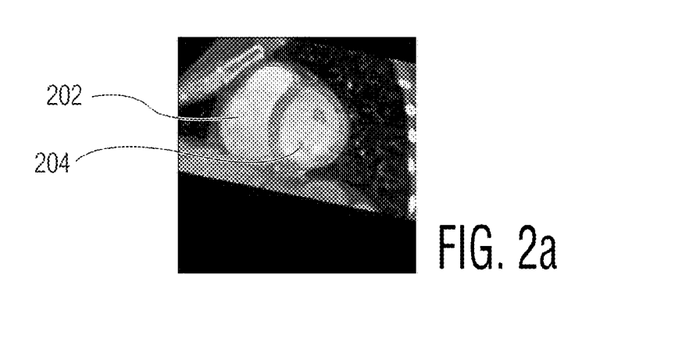
FIG. 2 illustrates examples of complete segmentation of all four chambers of a heart in a three dimensional medical image in accordance with the present invention.
Figure 2B:
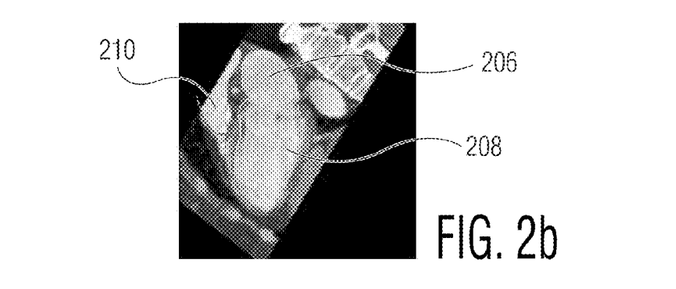
Figure 2C:
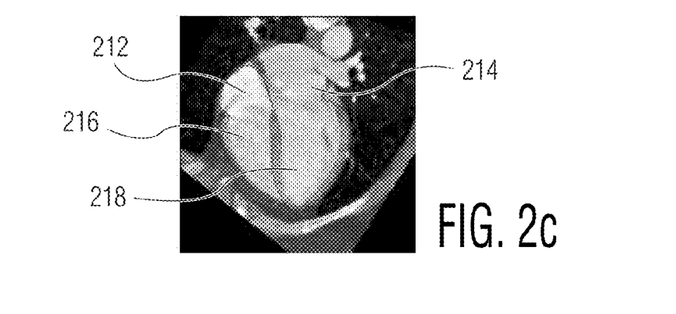
Figure 2D:
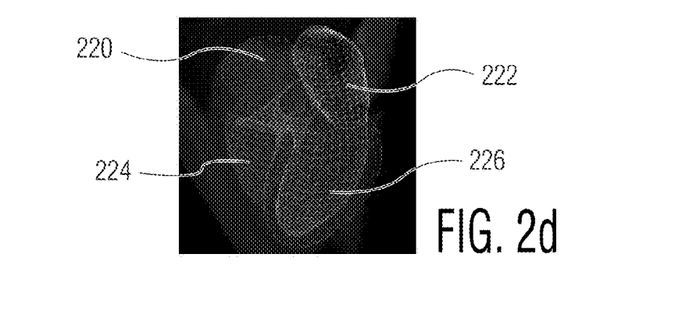

The present invention is directed to a system and method for multi-chamber heart segmentation. FIG. 1 illustrates a system 100 for segmenting a multi-chamber heart in three dimensional medical images according to an exemplary embodiment of the present invention. As shown in FIG. 1, the system 100 includes an acquisition device 105, a personal computer (PC) 110 and an operator's console 115 connected over a wired or wireless network 120.

The acquisition device 105 may be a computed tomography (CT) imaging device or any other three-dimensional (3D) high-resolution imaging device such as a magnetic resonance (MR) scanner or ultrasound scanner.

The PC 110, which may be a portable or laptop computer, a medical diagnostic imaging system or a picture archiving communications system (PACS) data management station, includes a central processing unit (CPU) 125 and a memory 130 connected to an input device 150 and an output device 155. The CPU 125 includes a multi-chamber heart segmentation module 145 that includes one or more methods for segmenting a heart in three dimensional medical images to be discussed hereinafter. Although shown inside the CPU 125, the multi-chamber heart segmentation module 145 can be located outside the CPU 125.

The memory 130 includes a random access memory (RAM) 135 and a read-only memory (ROM) 140. The memory 130 can also include a database, disk drive, tape drive, etc., or a combination thereof. The RAM 135 functions as a data memory that stores data used during execution of a program in the CPU 125 and is used as a work area. The ROM 140 functions as a program memory for storing a program executed in the CPU 125. The input 150 is constituted by a keyboard, mouse, etc., and the output 155 is constituted by a liquid crystal display (LCD), cathode ray tube (CRT) display, printer, etc.

The operation of the system 100 can be controlled from the operator's console 115, which includes a controller 165, e.g., a keyboard, and a display 160. The operator's console 115 communicates with the PC 110 and the acquisition device 105 so that image data collected by the acquisition device 105 can be rendered by the PC 110 and viewed on the display 160. The PC 110 can be configured to operate and display information provided by the acquisition device 105 absent the operator's console 115, by using, e.g., the input 150 and output 155 devices to execute certain tasks performed by the controller 165 and display 160.

The operator's console 115 may further include any suitable image rendering system/tool/application that can process digital image data of an acquired image dataset (or portion thereof) to generate and display images on the display 160. More specifically, the image rendering system may be an application that provides rendering and visualization of medical image data, and which executes on a general purpose or specific computer workstation. The PC 110 can also include the above-mentioned image rendering system/tool/application.

In accordance with an embodiment of the present invention, a system and method for automatic segmentation of 3D cardiac images is disclosed. Learned discriminative object models are used to exploit a large database of annotated 3D medical images. The segmentation is performed in two steps: anatomical structure localization and boundary delineation. Marginal Space Learning (MSL) is used to solve the 9-dimensional similarity search problem for localizing the heart chambers. MSL reduces the number of testing hypotheses by about six orders of magnitude as will be described in greater detail hereinafter. Steerable image features which incorporate orientation and scale information into the distribution of sampling points allow for the avoidance of time-consuming volume data rotation operations. After determining the similarity transformation of the heart chambers, the 3D shape is estimated through learning-based boundary delineation.

FIG. 2 illustrates examples of complete segmentation of all four chambers of a heart in a three dimensional medical image in accordance with the present invention. Segmentation of all four chambers of the heart can help to diagnose a variety of cardiac diseases, e.g., left atrium fibrillation or right ventricle overload. Each chamber can be identified by having it outlined either in a different color or by using different line thicknesses, hash marks or other distinguishing notations to differentiate one chamber from another. Because each image shows the heart from a different orientation, in each image only some of the chambers are visible. In FIG. 2(*a*), the right ventricle (RV) 202 and the left ventricle (LV) 2 are shown. With respect to LV 204, in accordance with an embodiment of the invention, both the endocardial surface and the epicardial surface can be identified.

FIG. 2(*b*) shows a view of the heart that has the left atrium (LA) 206, a portion of RV 210 and the LV 208. FIG. 2(*c*) shows a view of the heart that shows all four chambers of the heart: RA 212, LA 214, RV 216 and LV 218. FIG. 2(*d*) shows a 3D mesh image of the image shown in FIG. 2(*c*). Again, FIG. 2(*d*) shows all four chambers of the heart: RA 220, LA 222, RV 224, and LV 226.

MSL incrementally learns classifiers on projected sample distributions. As the dimensionality increases, the valid or positive space region becomes more restricted by previous marginal space classifiers. The estimation is split into three problems: translation estimation, translation-orientation estimation, and full similarity estimation.

Figure 3:
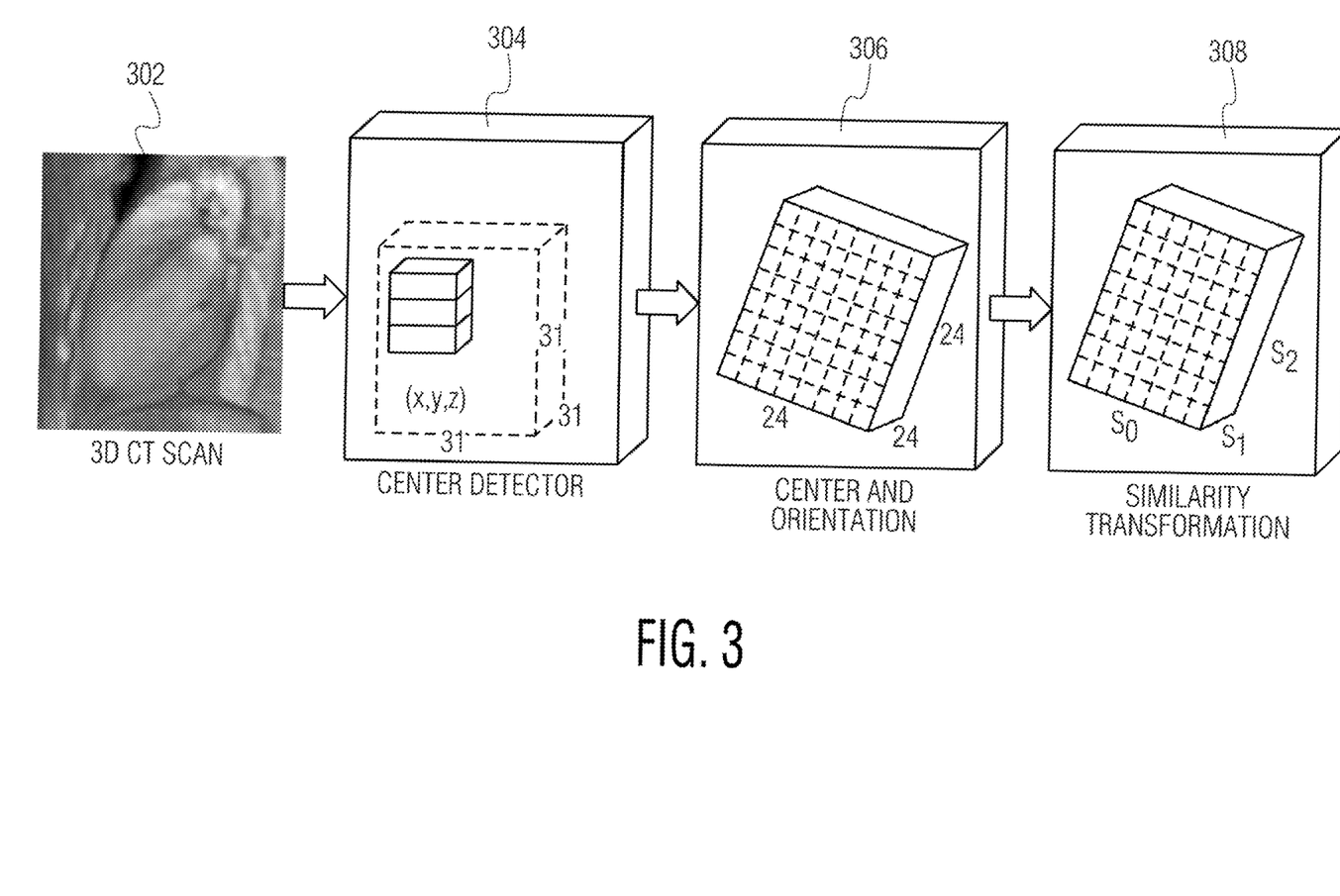
FIG. 3 is a functional block diagram that illustrates the steps performed to search for the center of the shape using marginal space learning in accordance with an aspect of the present invention.

FIG. 3 is a functional block diagram that illustrates the steps performed to search for the pose of the shape using marginal space learning in accordance with an aspect of the present invention. First a scanned 3D image of a heart is received at 302. Next, MSL is used to detect the center of the heart at 304. A second MSL estimation is used to identify the correct center and orientation of the image at 306. Then, a full similarity transformation is estimated for the image at 308. After each step of the process, multiple candidates are maintained to increase the robustness of the results.

Another advantage to using MSL for shape detection is that different features or learning methods can be used at each step. For example, in the translation estimation step rotation is treated as an intra-class variation so 3D Haar features can be used for detection. In the translation-orientation and similarity transformation estimation steps, steerable features are used which will be described in further detail hereinafter. Steerable features have a very flexible framework in which a few points are sampled from the volume under a special pattern. A few local features are extracted for each sampling point, such as voxel intensity and gradient. To evaluate the steerable features under a specified orientation, only the sampling pattern needs to be steered and no volume rotation is involved.

After the similarity transformation estimation, an initial estimate of the non-rigid shape is obtained. Learning based 3D boundary detection is used to guide the shape deformation in the active shape model framework. Again, steerable features are used to train local detectors and find the boundary under any orientation, therefore avoiding time consuming volume rotation.

In many instances, the posterior distribution or the object to be detected, e.g., heart, is clustered in a small region in the high dimensional parameter space. It is not necessary to search the whole space uniformly and exhaustively. In accordance with an embodiment of the present invention, an efficient parameter search method, Marginal Space Learning (MSL), is used to search such clustered space. In MSL, the dimensionality of the search space is gradually increased. For purposes of explanation, Q is the space where the solution to the given problem exists and $P_\Omega$ is the true probability that needs to be learned. The learning and computation are performed in a sequence of marginal spaces $$\Omega_1 \subset \Omega_2 \subset \ldots \subset \Omega_n = \Omega \quad (1)$$

such that $\Omega_1$ is a low dimensional space (e.g., a 3D translation instead of a 9D similarity transformation), and for each k, dim $(\Omega_k)$-dim$(\Omega_{k-1})$ is small. A search in the marginal space $\Omega_1$ using the learned probability model finds a subspace $\pi_1 \subset \Omega_1$ containing the most probable values and discards the rest of the space. The restricted marginal space $\Pi_1$ is then extended to $\Pi_1^l = \Pi_1 \times X_1 \subset \Omega_2$. Another stage of learning and testing is performed on $\Pi_1^l$ obtaining a restricted marginal space $\Pi_2 \subset \Omega_2$ and the procedure is repeated until the full space $\Omega$ is reached. At each step, the restricted space $\Pi_k$ is one or two orders of magnitude smaller than it $\Pi_{k-1} \times X_k$. This results in a very efficient method with minimal loss in performance.

Figure 4:
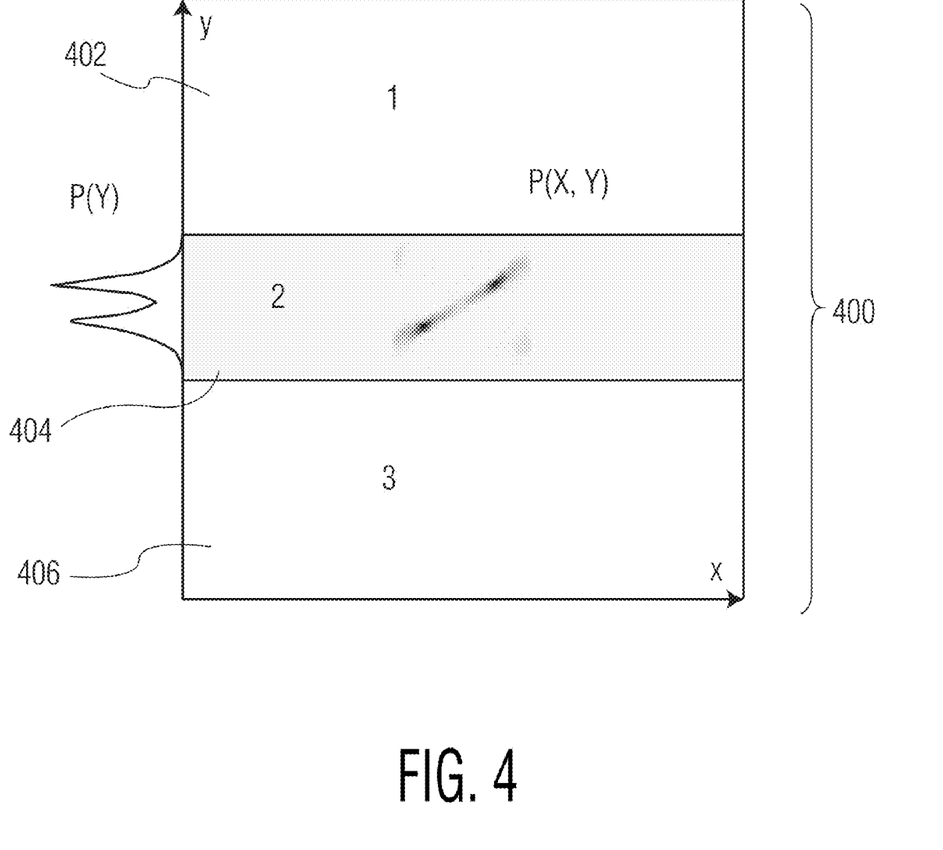
FIG. 4 illustrates an example of marginal space learning using a two dimensional space sample.

FIG. 4 illustrates a simple example of MSL using a 2D space sample. A classifier trained on p(y) can quickly eliminate a large portion of the search space 400. A classifier can then be trained in a much smaller region 404 of the image space for point distribution p(x, y) thereby eliminating the need search regions 402 and 406. Another classifier is then trained on restricted space region 404 for p(x, y).

Global features, such as 3D Haar wavelet features, are effective to capture the global information (e.g., orientation and scale) of an object. Prealignment of the image or volume is important for a learning based approach. However, it is very time consuming to rotate a 3D image, so 3D Haar wavelet features are not efficient for orientation estimation. Local features are fast to evaluate but they lose the global information of the whole object. A new framework, steerable features, can capture the orientation and scale of the object and at the same time is very efficient.

Figure 5A:
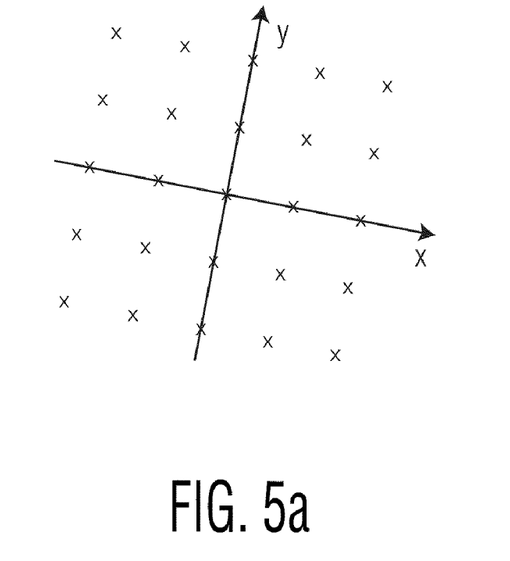
FIGS. 5a and 5b illustrate sampling features in steerable features in accordance with an aspect of the present invention.
Figure 5B:
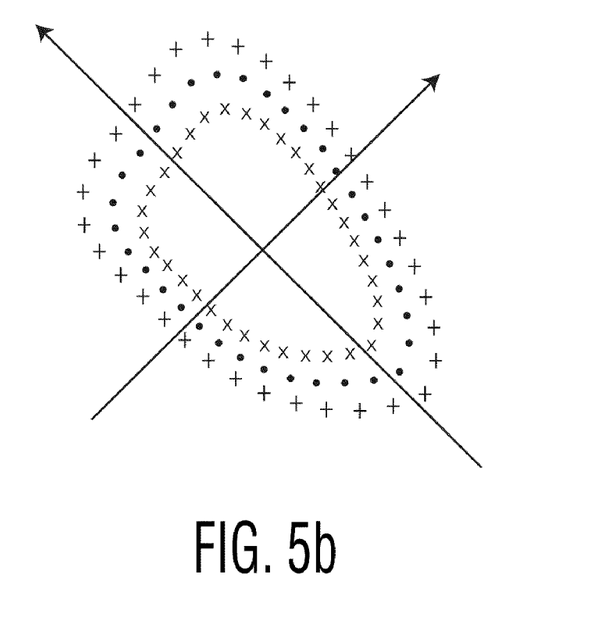

A few points from the image are sampled under a special pattern. A few local features are extracted for each sampling point, such as voxel intensity and gradient. FIG. 5a shows a regular sampling pattern. The sampling pattern can be used to test if a particular hypothesis is a good estimation of the similarity transformation of the object in the image. For example, suppose the hypothesis is $(X, Y, Z, \psi, \phi, \theta, S_x, S_y, S_z)$. A local coordinate system is centered on the candidate position (X, Y, Z) and the axes are aligned with the hypothesized orientation $(\psi, \phi, \theta)$. A few points are sampled along each coordinate axis inside a rectangle which is represented as "x". The sampling step along an axis is proportional to the scale $(S_x, S_y, S_z)$ of the shape in that direction to incorporate the scale information. The steerable features are a general framework and different sampling patterns can be defined depending on the application to incorporate the orientation and scale information. For many shapes, since the boundary provides critical information about the orientation and scale, sampling points are strategically put around the boundary, as shown in FIG. 5b.

For each sampling point, a set of local features are extracted based on the intensity and the gradient. For example, given a sampling point (x, y, z), if its intensity is I and the gradient is $g=(g_x, g_y, g_z)$, the following features are used: I, $\sqrt{I}$, $I^2$, $I^3$, log I, $g_x$, $g_y$, $g_z$, $\|g\|$, $\sqrt{\|g\|}$, $\|g\|^2$, $\|g\|^3$, log$\|g\|$, ..., etc. In total, there are 24 local features for each sampling point. If there are P sampling points (often in the order of a few hundreds to a thousand), a feature pool containing 24×P features is obtained. These features are used to train simple classifiers and a Probabilistic Boosting Tree (PBT) is used to combine the simple classifiers to get a strong classifier for the given parameters.

Instead of aligning the volume to the hypothesized orientation to extract Haar wavelet features, the sampling pattern is steered, hence the name "steerable features". In the steerable feature framework, each feature is local, therefore efficient. The sampling pattern is global to capture the orientation and scale information. In this way, it combines the advantages of both global and local features.

Figure 8:
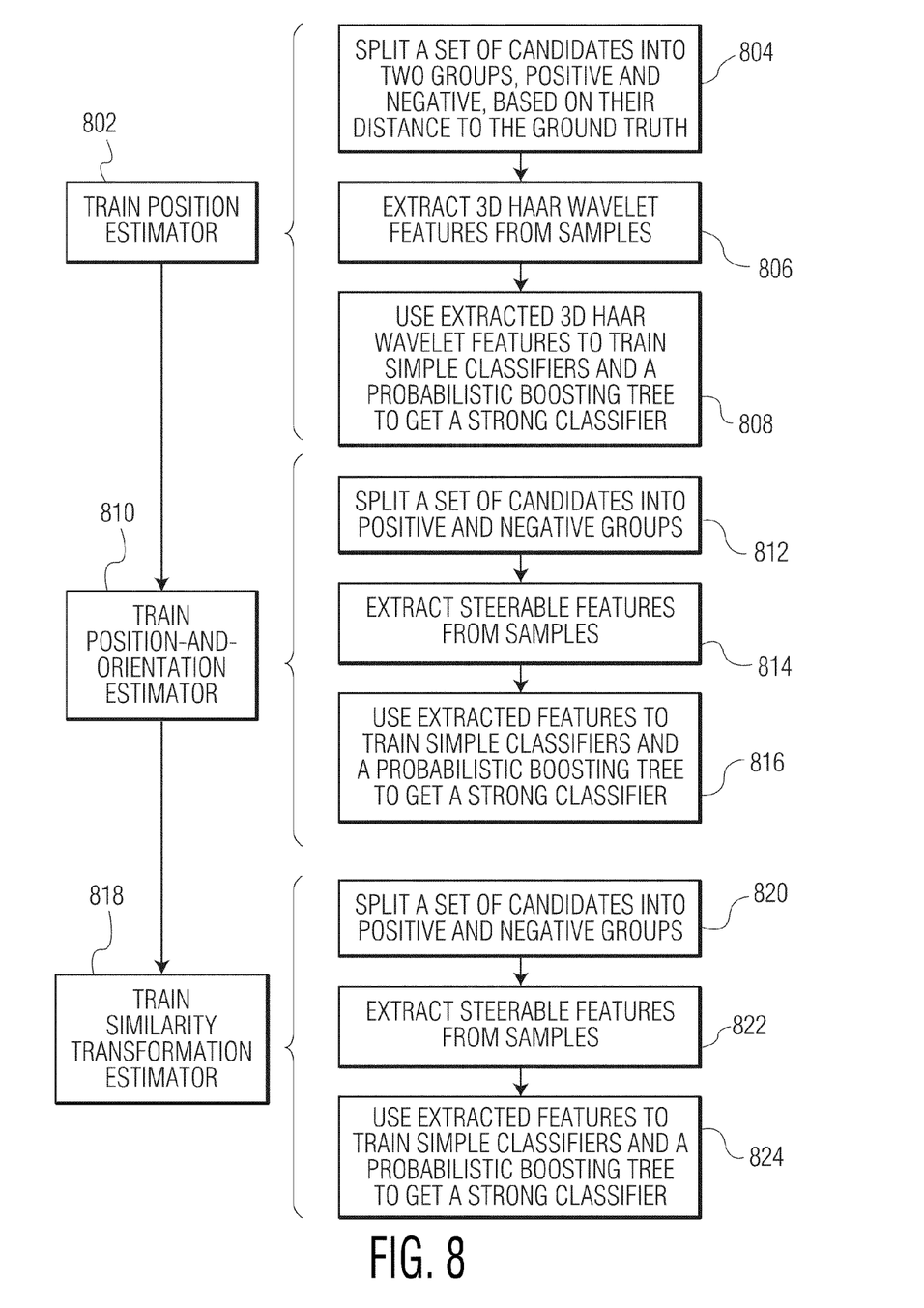
FIG. 8 is a flow chart that outlines method for segmenting chambers of a heart in accordance with the present invention.

In accordance with an embodiment of the present invention, a method for segmenting chambers of a heart using a 3D object localization scheme using MSL and steerable features will be described with reference to FIG. 8. As shown in FIG. 8, the position of the object in the image is estimated (step 802). The orientation and scale are treated as intra-class variations, therefore learning is constrained in a marginal space with three dimensions. Haar wavelet features are very fast to compute and have been shown to be effective for many applications. Therefore, 3D Haar wavelet features can be used for learning in this step.

Given a set of candidates, they are split into two groups, positive and negative, based on their distance to the ground truth (step 804). The error in object position and scale estimation is not comparable with that of orientation estimation directly. Therefore, a normalized distance measure is defined using the searching step size.

$$E = \max_{i=1,\ldots,n} |V_i^t - V_i^t| / SearchStep_i \quad (2)$$

where $V_i^t$ is the estimated value for dimension i and $V_i^t$ is the ground truth. A sample is regarded as a positive one if $E \leq 1.0$ and all the others are negative samples. The searching step for position estimation is one voxel, so a positive sample (X, Y, Z) should satisfy $$\max\{|X-X_i|, |Y-Y_i|, |Z-Z_i|\} \leq 1 \text{ voxel} \quad (3)$$

where $(X_i, Y_i, Z_i)$ is the ground truth of the object center.

Given a set of positive and negative training samples, 3D Haar wavelet features are extracted (step 806) and a classifier is trained using the probabilistic boosting tree (PBT) (step 808). Given a trained classifier, a training volume is scanned and a small number of candidates (e.g., 100) are preserved such that the solution is among top hypotheses.

An example of how position-orientation and similarity transformation estimators are trained (step 810) will now be described. For a given volume, 100 candidates $(X_i, Y_i, Z_i)$, i=1, . . . , 100 exist for the object position. The position and orientation are then estimated. The hypothesized parameter space is six dimensional so the dimension of the candidates needs to be augmented. For each candidate of the position, the orientation space is scanned uniformly to generate the hypotheses for orientation estimation. It is well known that the orientation in 3D can be represented as three Euler angles, $\psi$, $\phi$, and $\theta$. The orientation space is scanned using a step size of 0.2 radians (i.e., 11 degrees). It is to be understood by those skilled in the art that a different scanning rate can be used without departing from the scope or spirit of the present invention.

For each candidate $(X_i, Y_i, Z_i)$, it is augmented with N (e.g., about 1000) hypotheses about orientation, $(X_i, Y_i, Z_i, \psi_j, \phi_j, \theta_j)$, j=1 . . . N. Some hypotheses are close to the ground truth (positive) and others are far away (negative). The learning goal is to distinguish the positive and negative samples using image features, i.e., steerable features. A hypothesis (X, Y, Z, $\psi$, $\phi$, $\theta$) is regarded as a positive sample if it satisfies both Eq. 3 and $$\max\{|\psi-\psi_i|, |\phi-\phi_i|, |\theta-\theta_i|\} \leq 0.2 \quad (4)$$

where ($\psi_i$, $\phi_i$, $\theta_i$) represent the orientation ground truth. All the other hypotheses are regarded as negative samples.

Since aligning 3D Haar wavelet features to a specified orientation is not efficient, steerable features are used in the following steps. A classifier is trained using PBT and steerable features. The trained classifier is used to prune the hypotheses to preserve only a few candidates.

The similarity estimation step in which scale is added is similar to the position-orientation transformation except learning is performed on the full nine dimensional similarity transformation space. The dimension of each candidate is augmented by scanning the scale subspace uniformly and exhaustively.

Now the testing procedure on an unseen volume will be described. The input volume is first normalized to 3 mm isotropic resolution, and all voxels are scanned using the trained position estimator. A predetermined number of top candidates (e.g., 100), ($X_i$, $Y_i$, $Z_i$), i=1 ... 100, are kept. Each candidate is augmented with N (e.g., 1000) hypotheses about orientation, ($X_i$, $Y_i$, $Z_i$, $\psi_j$, $\phi_j$, $\theta_j$), j=1 ... N. Next, the trained translation-orientation classifier is used to prune these 100×N hypotheses and the top 50 candidates are retained, ($\hat{X}_i$, $\hat{Y}_i$, $\hat{X}_i$, $\hat{\psi}_i$, $\hat{\phi}_i$, $\hat{\theta}_i$), i=1 ... 50. Similarly, each candidate is augmented with M (also about 1000) hypotheses about scaling and use the trained classifier to rank these 50×M hypotheses. The goal is to obtain a single estimate of the similarity transformation. In order to aggregate the multiple candidates, averaging of the top K (K=100) is performed.

In terms of computational complexity, for translation estimation, all voxels are scanned (about 260,000 for a small 64×64×664 volume at the 3 mm resolution) for possible object position. There are about 1000 hypotheses for orientation and scale each. If the parameter space is searched uniformly and exhaustively, there are about $2.6 \times 10^{11}$ hypotheses to be tested. By using MSL, only $4.1 \times 10^5$ (260,000+ 100×1000+50×1000) hypotheses are tested and the amount of testing is reduced by almost six orders of magnitude.

Figure 6A:
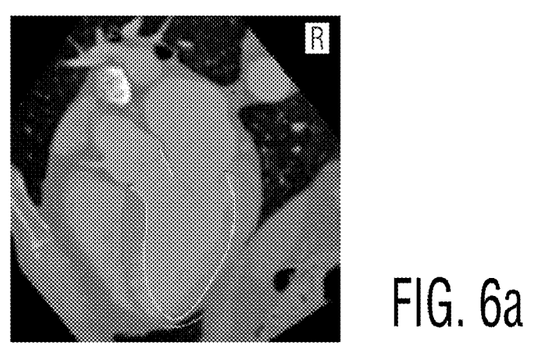
FIGS. 6a-6c illustrate examples of non-rigid deformation estimation for a left ventricle.

After the first stage, the position, orientation and scale of the object are obtained. The mean shape is aligned with the estimated transformation to get a rough estimate of the object shape. FIG. 6a shows an aligned left ventricle for heart chamber segmentation in a cardiac CT image.

Figure 6B:
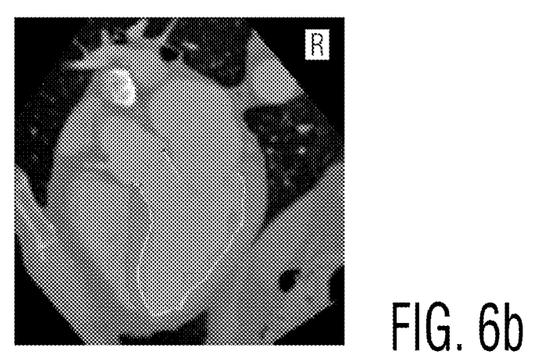
Figure 6C:
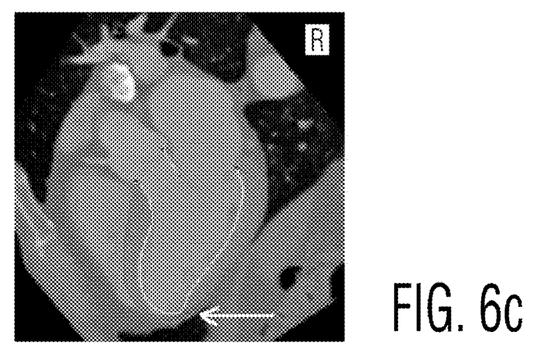

A set of local boundary detectors are trained using the steerable features with the regular sampling pattern (as shown in FIG. 5a). The boundary detectors are then used to move each landmark point to the optimal position where the estimated boundary probability is maximized. Since more accurate delineation of the shape boundary is desired, this stage is performed on the original high resolution image. FIG. 6b shows the adjusted shape of the left ventricle, which follows the boundary well but is not smooth and an unnatural shape may be generated. Shape constraint is enforced by projecting the adjusted shape onto a shape subspace to get the final result as shown in FIG. 6c. The arrow in FIG. 6c indicates the region with better boundary delineation.

Figure 7A:
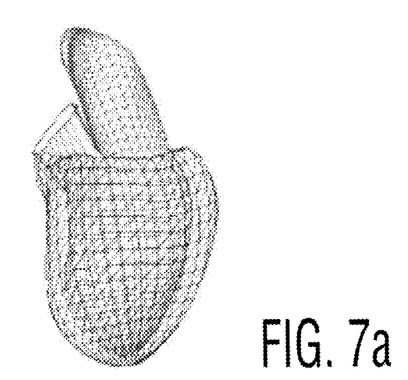
FIGS. 7a-7c illustrate a triangulated heart surface model of various heart chambers.
Figure 7B:
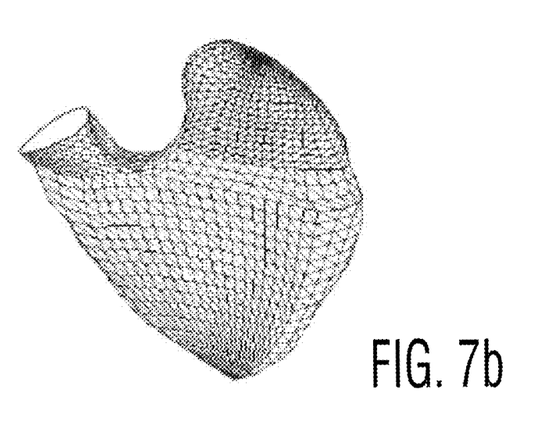
Figure 7C:
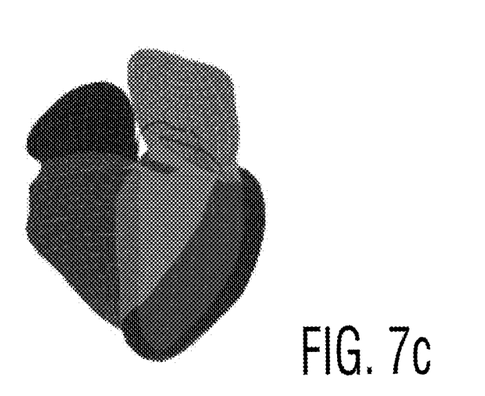

An example will now be described which demonstrates the performance of the proposed method for multi-chamber localization and delineation in cardiac CT images. As shown in FIGS. 7a-7c, triangulated surface meshes are used to represent the anatomical structures. FIG. 7a illustrates a triangulated surface mesh model of the left ventricle and the left atrium. FIG. 7b illustrates a triangulated surface mesh model of the right ventricle and right atrium. FIG. 7c illustrates the combined four chamber model. In the models, both the endo- and epi-cardial surfaces for, the left ventricle are delineated, but only the endocardial surface is delineated for the other chambers. During manual labeling, correspondence is established between mesh points crossing images, therefore, the statistical shape model for ASM can be built.

Having described embodiments for a system and method for segmenting chambers of a heart in a three dimensional image, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters set forth in the appended claims.

We claims:

1. A method for segmenting chambers of a heart in three dimensional images comprising the steps of:
   receiving a set of three dimensional images of a heart;
   estimating a position of the heart in the three dimensional images;
   using Marginal Space Learning (MSL) to constrain searching space to three dimensions;
   identifying a set of candidate locations in the images;
   dividing the candidates into positive and negative groups based on their distance from the estimated position of the heart; and
   training the classifier using the positive and negative candidates to identify a subset of candidates that likely coincide with the location of the heart, wherein said subset of candidates localizes the shape of the heart in the three dimensional images; and
   identifying boundaries of the chambers of the heart in the localized shape using steerable features.

2. The method of claim 1 further comprising the step of:
   tracking motion of the shape of the heart in the images through a cardiac cycle.

3. The method of claim 1 wherein the step of identifying boundaries of the chambers of the heart further comprises the steps of:
   estimating possible orientations of each of the subset of candidates;
   training a classifier to determine which orientations may be valid;
   estimating scale for those candidates having valid orientations;
   using the position, orientation and scale to obtain a rough estimate of the mean shape of the heart; and
   using landmark points to identify the shape boundaries of each heart chamber.

4. The method of claim 3 wherein the orientations of each subset of candidates is done using steerable features.

5. The method of claim 3 wherein a Probabilistic Boosting Tree is used to train the classifier.

6. The method of claim 3 wherein the step of estimating the scale uses a nine dimensional similarity transformation space.

7. The method of claim 1 wherein 3D Haar wavelet features are used to constrain the image to three dimensions.

8. The method of claim 1 wherein the classifiers are trained using a Probabilistic Boosting Tree.

9. The method of claim 1 wherein the three dimensional images are computed tomography images.

10. A system for segmenting heart chambers in three dimensional images comprising:
    an acquisition device for acquiring three dimensional images of a heart;
    a processor that receives the acquired three dimensional images of the heart, the processor performing a method for segmenting the heart chambers in the three dimensional images, the method comprising the steps of:
estimating a position of the heart in the three dimensional images;
using Marginal Space Learning (MSL) to constrain searching space to three dimensions;
identifying a set of candidate locations in the images;
dividing the candidates into positive and negative groups based on their distance from the estimated position of the heart; and
training the classifier using the positive and negative candidates to identify a subset of candidates that likely coincide with the location of the heart, wherein said subset of candidates localizes the shape of the heart in the three dimensional images; and
identifying boundaries of the chambers of the heart in the localized shape using steerable features; and
a display for displaying the segmented chambers of the heart.

11. The system of claim 10 wherein said processor further performs the step of:
tracking motion of the shape of the heart in the images through a cardiac cycle.

12. The system of claim 10 wherein the step of identifying boundaries of the chambers of the heart further comprises the steps of:
estimating possible orientations of each of the subset of candidates;
training a classifier to determine which orientations may be valid;
estimating scale for those candidates having valid orientations;
using the position, orientation and scale to obtain a rough estimate of the mean shape of the heart; and
using landmark points to identify the shape boundaries of each heart chamber.

13. The system of claim 12 wherein the orientations of each subset of candidates is done using steerable features.

14. The system of claim 12 wherein a Probabilistic Boosting Tree is used to train the classifier.

15. The system of claim 12 wherein the step of estimating the scale uses a nine dimensional similarity transformation space.

16. The system of claim 10 wherein 3D Haar wavelet features are used to constrain the image to three dimensions.

17. The system of claim 10 wherein the classifiers are trained using a Probabilistic Boosting Tree.

18. The system of claim 10 wherein the three dimensional images are computed tomography images.

* * * * *